United States Patent
Krishnamachari et al.

(10) Patent No.: US 8,253,937 B2
(45) Date of Patent: Aug. 28, 2012

(54) OPTICAL EVALUATION METHOD BY MEANS OF LASER PULSES AND CORRESPONDING APPARATUS

(75) Inventors: Vishnu Vardhan Krishnamachari, Mannheim (DE); William C. Hay, Heppenheim (DE); Volker Seyfried, Nussloch (DE); Bernd Widzgowski, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 162 days.

(21) Appl. No.: 12/626,057

(22) Filed: Nov. 25, 2009

(65) Prior Publication Data

US 2010/0134793 A1    Jun. 3, 2010

(30) Foreign Application Priority Data

Nov. 28, 2008    (DE) .................. 10 2008 059 579

(51) Int. Cl.
G01J 3/44    (2006.01)
(52) U.S. Cl. ....................................... 356/301
(58) Field of Classification Search .......... 356/301, 356/318, 72–73
See application file for complete search history.

(56) References Cited

U.S. PATENT DOCUMENTS

| | | | |
|---|---|---|---|
| 4,990,740 A * | 2/1991 | Meyer | 219/121.52 |
| 2006/0066848 A1 | 3/2006 | Frankel | |
| 2007/0159690 A1* | 7/2007 | Ulrich et al. | 359/385 |

OTHER PUBLICATIONS

Krampert, Gerhard: Femtosecond Quantum Control and Adaptive Polarization Pulse Shaping; Wuerzburg 2004.
Seifert, G., Patzlaff, T., Graener, H.: Observation of Low-Frequency Raman and Kerr Effect Contributions in Picosecond Infrared Pump Probe Experiments; Vibrational Spectroscopy 23 (2000) 219-230; PII: S0924-2031 (00)00064-3.
Haran, Gilad, Sun, Wei-Dong, Wynne, Klaas, Hochstrasser, Robin M.: Femtosecond Far-Infrared Pump-Probe Spectroscopy: A New Tool for Studying Low-Frequency Vibrational Dynamics in Molecular Condensed Phases; Chemical Physics Letters 274 (1997) 365-371; PII S0009-2614(97)00705-7.
E. Rettweger, et al., "Fluorescence Depletion Mechanisms in Super-Resolving STED Microscopy", Chemical Physics Letters 442, Feb. 22, 2007, pp. 483-487, Elsevier B.V.

* cited by examiner

*Primary Examiner* — Tarifur Chowdhury
*Assistant Examiner* — Abdullahi Nur
(74) *Attorney, Agent, or Firm* — Schlee IP International, P.C.; Alexander R. Schlee

(57) ABSTRACT

An optical evaluation method and an apparatus for performing said method are described. First laser pulses of a first type and second laser pulses of a second type that differs from the first type are sent onto a sample to be examined. The sample is hit with first incident light from the two laser pulses in at least one manner of simultaneously, within a very short time lag between the two laser pulses, and a time-correlated manner of the two laser pulses, thereby generating a first optical signal, and hit with second incident light from the two laser pulses, thereby generating a second optical signal. The generated first and second optical signals are detected with at least one detector; and an electronic difference between the first and second optical signals is generated.

12 Claims, 6 Drawing Sheets

OPTICAL EVALUATION METHOD BY MEANS OF LASER PULSES AND CORRESPONDING APPARATUS

CROSS-REFERENCE TO RELATED APPLICATION

This application claims the priority of the German patent application DE 102008059579.9 having a filing date of Nov. 28, 2008. The entire content of this prior German patent application DE 102008059579.9 is herewith incorporated by reference.

BACKGROUND OF THE INVENTION

The invention relates to an optical evaluation method by means of laser pulses as well as to a corresponding apparatus.

A large number of optical measuring methods is known in which a sample interacts with laser light from different laser sources (excitation light), and as a result of this interaction an optical signal, for example, light of a different color or wavelength, polarization, intensity or the like, is generated and can be detected. Due to the position-dependent detection of the detection light, such methods can be used inter alia for imaging, for example in microscopy. Examples thereof are mainly methods which make use of frequency doubling, frequency multiplication, sum frequency mixing, difference frequency mixing, four-wave-mixing, CARS (Coherent anti-Stokes Raman Spectroscopy), FM-CARS, OCT, stimulated fluorescence, stimulated Raman scattering, i.e. stimulated Raman gain or stimulated Raman loss etc.

From Chem. Phys. Lett. 2007, 442, 483-487, an optical evaluation method is known, in which the effect of stimulated fluorescence is made use of. Here, fluorescent dyes are first placed in an excited state by a first laser pulse. When a second laser pulse of a suitable wavelength is irradiated within a very short time lag, i.e. within some nanoseconds, this second excitation laser pulse is amplified by the excited dyes, and a detection light is generated which, however, due to the same wavelength can only hardly be distinguished from the excitation light. On a suitable detector, an optical signal is detected which, given an incidence of the two laser pulses at the sample within a very short time lag, differs from the signal which would be generated when both laser pulses would not be incident on the sample within a very short time lag. In this specific case, the first laser pulse is already suppressed upstream of the detector by means of suitable spectral filters so that exclusively the second laser pulse as well as the additionally generated optical signal arrive at the detector. In order to only obtain the desired additional optical signal, one would have to make a measurement with the first excitation laser pulse and a measurement without the first excitation laser pulse, and to form the respective difference. However, the two measurements differ from one another so little (in the order of less than $10^{-8}$) that due to the limited dynamic range of the detectors or due to detection noise etc. the desired optical signal can no longer be perfectly detected. Therefore, in such cases as well as in the cited publication usually the known lock-in technology is used with the aid of which the desired signal can still be separated from the background.

A disadvantage of this lock-in technology is, however, the limited speed which represents a clear disadvantage in particular for imaging methods such as laser scanning technologies. In particular, when used in laser scanning microscopy, where frame rates of up to 25 frames/second given image sizes of 512×512 pixels are common, wherein for individual pixels then only times of clearly less than 1 microsecond are available, the use of this technology would result in a clear slowing down of the image taking, which—at least for the examination of processes in living cells—is inacceptable.

SUMMARY OF THE INVENTION

It is the object of the invention to specify an optical evaluation method and an apparatus, which remove the disadvantages of the prior art.

This object is solved by an optical evaluation method, comprising: directing first laser pulses of a first type and second laser pulses of a second type that differs from the first type onto a sample to be examined; hitting the sample with first incident light from the two laser pulses in at least one manner of simultaneously, within a very short time lag between the two laser pulses, and a time-correlated manner of the two laser pulses, thereby generating a first optical signal; hitting the sample with second incident light from the two laser pulses in at least one manner of non-simultaneously, not within a very short time lag between the two laser pulses, and a non-time-correlated manner of the two laser pulses, thereby generating a second optical signal; detecting the generated first and second optical signals with at least one detector; and generating an electronic difference between the first and second optical signals.

This object is further solved by an apparatus for performing the aforementioned method of evaluating laser pulses, comprising: a first laser that generates first laser pulses of a first type; a second laser that generates second laser pulses of a second type that differs from the first type; a light directing unit for directing the first laser pulses and the second laser pulses onto a sample to be examined, the light directing unit being configured to hit the sample with first incident light from the two laser pulses in at least one manner of simultaneously, within a very short time lag between the two laser pulses, and a time-correlated manner of the two laser pulses, thereby generating a first optical signal; and to hit the sample with second incident light from the two laser pulses in at least one manner of non-simultaneously, not within a very short time lag between the two laser pulses, and a non-time-correlated manner of the two laser pulses, thereby generating a second optical signal; a first detector for detecting the generated first and second optical signals with at least one detector; and an electronic signal processing unit generating an electronic difference between the first and second optical signals.

The present invention solves the given problem in the case that the optical signal to be detected is generated by the interaction of the sample with laser pulses of at least two different types, the optical signal desired for the detection only being generated when the arrival of the two types of excitation pulses has a specific temporal connection, for example in that the two pulses arrive at the sample simultaneously or within a very short time lag or have a specific predetermined time lag (time-correlated pulses). Examples thereof are e.g. sum frequency mixing and difference frequency mixing, in which the detection light has a different wavelength than the excitation light. Others examples are CARS, stimulated fluorescence and stimulated Raman scattering, in which likewise two or more laser pulses interact simultaneously or within a very short time lag with the sample, not necessarily all these laser pulses being absorbed by the sample—in the latter cases pulses even being amplified by the sample so that the detection light cannot be distinguished from the excitation light and can only be detected by an amplification of the excitation light. For reasons of simplicity, however, in this context, excitation pulses are spoken about whenever the interaction of the two pulses with the sample results in the desired optical signal, even if the second excitation pulse, as in the case of stimulated fluorescence or stimulated Raman scattering, would rather be called a de-excitation pulse than an excitation pulse from a spectroscopic point of view.

DETAILED DESCRIPTION OF THE INVENTION

The present invention is based on the recognition to provide for the excitation pulses of both types pulse sequences with the aid of a suitable optical arrangement, in which pulse sequences the pulses of the two types are, on the one hand, partly incident simultaneously or within a very short time lag or in a time-correlated manner at the sample and are, on the other hand, partly not incident simultaneously or within a very short time lag or in a time-correlated manner. By means of this structure and the associated detection on one, two or more detectors together with a subsequent difference formation in a suitable arrangement, it is possible to achieve the desired signal quality already without using the lock-in technology often used in this field. What is not to be explicitly excluded here is, however, that the lock-in technology is nevertheless additionally used for further signal improvement.

In a typical inventive design, use is made, for example, of two temporally synchronized pulse lasers having different properties (e.g. different wavelengths or polarization) and having different repetition rates. For example, one of the two lasers has half the repetition rate of the other laser, which might be realized by halving the repetition rate, for example, with the aid of a pulse picker. What is achieved thereby is that only at every second pulse of the laser having the higher repetition rate, there is also a pulse of the other laser. As a result thereof, only every second time, the generated optical signal has the desired value which is extracted by way of difference formation with the respective other intermediate pulses. To this end, for example, the electronic signal, e.g. the current of the two detectors, is split into two branches, the current in one of the two branches is appropriately delayed and then the difference is electronically formed, e.g. by a push-pull detection circuit or difference detection circuit. As a result thereof, one obtains a sign-changing signal which exclusively contains the desired information and can suitably be further processed.

A preferred version is to rectify this signal by multiplication with a sign-changing digital signal, to possibly filter it with an adapted low pass filter and, subsequently, to digitize it.

There are numerous possibilities for generating suitable pulse sequences of the at least two excitation lasers. To this end, for example, the two lasers can be suitably electronically triggered. If, however, passively mode-coupled lasers or other lasers which cannot be triggered are concerned the synchronization of the laser pulses must be effected otherwise. For example, mechanisms with which also two passively mode-coupled lasers can be synchronized are known e.g. as synchro-lock. Another possibility is the use of the one laser as a pump source for the other one, as is, for example, realized given synchronously pumped lasers or optically parametric oscillators (OPO). A supercontinuum generation with broad wavelength spectrum with the same pump source and a subsequent filtering out of two wavelengths and/or the use of the pump wavelength together with the generated wavelengths results in a suitable synchronization.

In any case, however, now the suitable pulse sequences have to be generated, in which at specific times the two laser pulses occur simultaneously, synchronized within a very short time lag or in a time-correlated manner, and at specific times, this condition is just not met. For this, it is, for example, possible to set the repetition rates of the two lasers such that the repetition rate of the one laser is an integral multiple of the repetition rate of the other laser. Given a suitable temporal matching of the lasers, it is then guaranteed that e.g. certain pulses from the one laser are incident at the sample simultaneously with or within a very short time lag after pulses from the second laser, while for other pulses of the first laser, no pulse from the second laser is incident at the sample. As a result thereof, in the generated optical signal both time sections with the desired signal and time sections without the desired signal can be found so that by means of a suitable further processing by way of analog difference formation the desired signal can be determined background-free. For this, it is not essential that the two repetition rates are integral multiples of one another, also small rational multiples allow a similar signal evaluation. Thus, when the ratio of the repetition rates is chosen to be 2:3, one can, for example, achieve a simultaneous incidence or an incidence within a very short time lag of the pulses at the sample after every third pulse of the first or every second pulse of the second laser, so that, here too, a corresponding evaluation is possible.

As illustrated in the embodiments, an equidistant pulse sequence is not essential either. Instead, for example, double pulses etc. are quite advantageous at least for one of the two lasers. It is only important that during the irradiation of the pulse sequences from the two lasers there are both points in time or time sections at/in which the pulses from both lasers arrive at the sample simultaneously or within a very short time lag and at/in which the desired signal (plus background) is generated and points in time or time sections at/in which due to fact that the laser pulses do not arrive in a timely correct manner, the desired signal is not generated (i.e. only the background) so that later on with the aid of a suitable difference formation the desired signal can be extracted already prior to digitalization.

Particularly advantageous is of course when the pulse sequences are chosen such that in both partial signals which are subtracted from one another the intensity of the background signal is equal so that the background signal automatically completely disappears in the difference formation. However, in certain situations it is completely sufficient that the intensity ratio of the background signals in both partial signals is temporarily constant since then for example, by means of a suitable electronic circuit for attenuation or multiplication of one of the two partial signals, the condition of an equal intensity of the background in both partial signals can likewise be met.

For generating the suitable pulse sequences, it is, as stated, possible to use two synchronized lasers already having the correct pulse repetition rates. In many cases, however, it is particularly advantageous to choose as an initial pulse two lasers having the same repetition rate, for example two synchronized titan sapphire lasers or a laser which at the same time is used as a first laser, but, on the other hand, serves as a pump source for the second laser so that the first and second laser automatically have the same repetition rate. Examples of these are fiber lasers together with a crystal pumped by means of these fiber lasers or a super continuum fiber, pump sources together with the optical parametric oscillators (OPO) pumped by them etc. The joint use of signal and idler light of an OPO is likewise possible. What is common to all these laser pairs described is that they have the same repetition rate. In order to obtain the required laser pulse sequences herefrom, the pulse sequence of at least one of the two laser branches has to be modified. This can be done, for example, by means of a pulse picker, with the aid of which the repetition rate of one or both lasers is reduced. On the other hand, it is also possible to generate in one or both laser branches by way of beam splitting or beam re-combining additional pulses at arbitrary points in time and to generate the inventive pulse sequences in this way.

It is particularly advantageous when, in the inside of the respective laser pulse sequences of one of the two lasers those individual pulses that have a "partner" in the laser pulse sequence of the other laser stand out due to specific optical properties compared to the remaining laser pulses, e.g. by a changed polarization, a changed wavelength, or possibly even a different direction. In this case, it is then possible to separate the different portions of the generated optical signal later on by suitable means (e.g. polarization filters or color splitters or spatial separators) and thus, to separately detect the different portions of the signal with the aid of several detectors, which facilitates the downstream electronic evaluation.

In any case, at one or more detectors electronic signals are finally generated which have both time sections with the desired signal (plus background) as well as time sections without the desired signal (i.e. only background). Insofar as these signal portions are detected at different detectors, an electronic subtraction following a possible previous adaptation of the amplitude (due to differences, for example, in the sensitivity of the detectors or the circuitry) and a suitable temporary delay can be easily accomplished. But also given a detection with the aid of one single detector a corresponding electronic evaluation is likewise also possible. Here, however, the signal has to be subtracted from itself in a time-delayed manner so that here, too, the background is suppressed already before the further evaluation. This is explained in more detail in the embodiments.

The procedure as described is particularly suitable for a background-free detection of signals when the processes of frequency doubling, frequency multiplication, sum frequency mixing, difference frequency mixing, four-wave-mixing, CARS, FM-CARS, OCT, stimulated fluorescence, stimulated Raman scattering, i.e. stimulated Raman gain or stimulated Raman loss etc. are used for imaging in scanning systems such as laser scanning microscopes, confocal microscopes etc. In the following embodiments, the technology is explained in detail with reference to the examples of stimulated fluorescence as well as the two Raman techniques stimulated Raman gain and stimulated Raman loss in laser scanning microscopes for imaging. The transfer to the respective other techniques mentioned and respective other ones is of course analogously possible.

Embodiments of the invention are explained with reference to the drawings.

BRIEF DESCRIPTION OF THE DRAWINGS

FIG. 1 shows an apparatus according to the first embodiment in which the stimulated fluorescence is made use of.

DETAILED DESCRIPTION OF THE DRAWINGS

Figure 1:
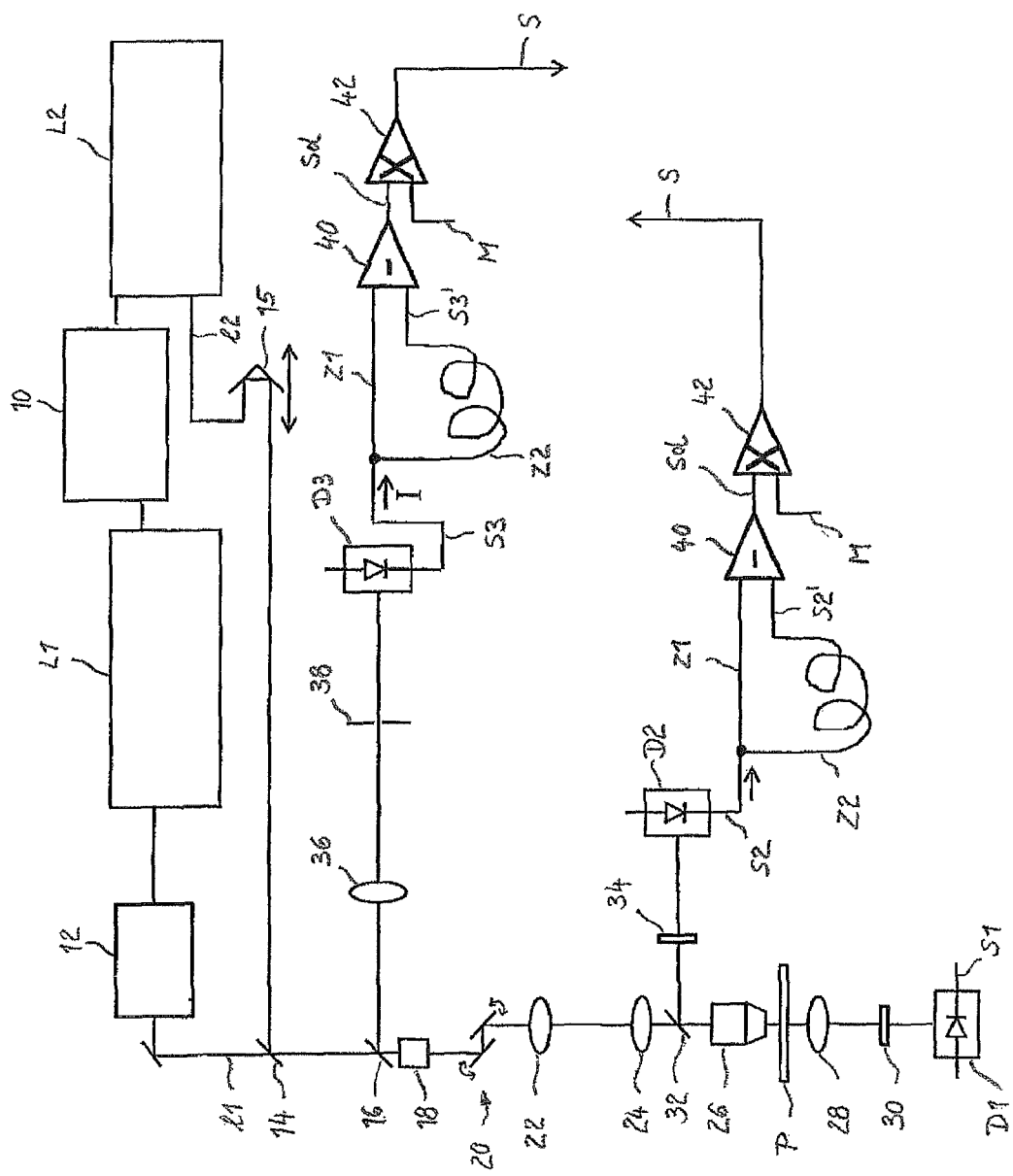

In the embodiment according to FIG. 1, the physical effect of stimulated fluorescence is made use of. This stimulated fluorescence is a photophysical process in which fluorescent molecules in a sample P are placed in a higher energy state by a first exciting laser pulse I1. When a second laser pulse I2 of suitable wavelength, preferably with a wavelength of the fluorescent radiation, arrives promptly, i.e. within a very short time lag, for example of a few nanoseconds or picoseconds, after the first laser pulse I1 at the sample P, then the process of stimulated fluorescence can take place. This means that the second laser pulse I2 can also use the excess energy present in the sample P due to the first laser pulse I1, and that the second laser pulse I2 exits the sample P amplified by a specific energy portion. When the first laser pulse I1 is switched off or given a too great time lag between the two laser pulses I1, I2, this amplification does not take place. A detector which only detects the wavelength of the second laser pulse I2 measures a slightly higher signal in the first case than in the second case. With the aid of the inventive apparatus or, respectively, the associated method, the respective signal differences can be detected with sufficient accuracy so that the amount of amplification or the excess in radiation can be determined free of background radiation and disturbing radiation and is directly available as a local sample parameter for the imaging. The example according to FIG. 1 can also be used for other types of luminescence, for example the phosphorescence, wherein the time lag between the laser pulses then has to be chosen longer, for example in the micro or millisecond range.

Figure 2:
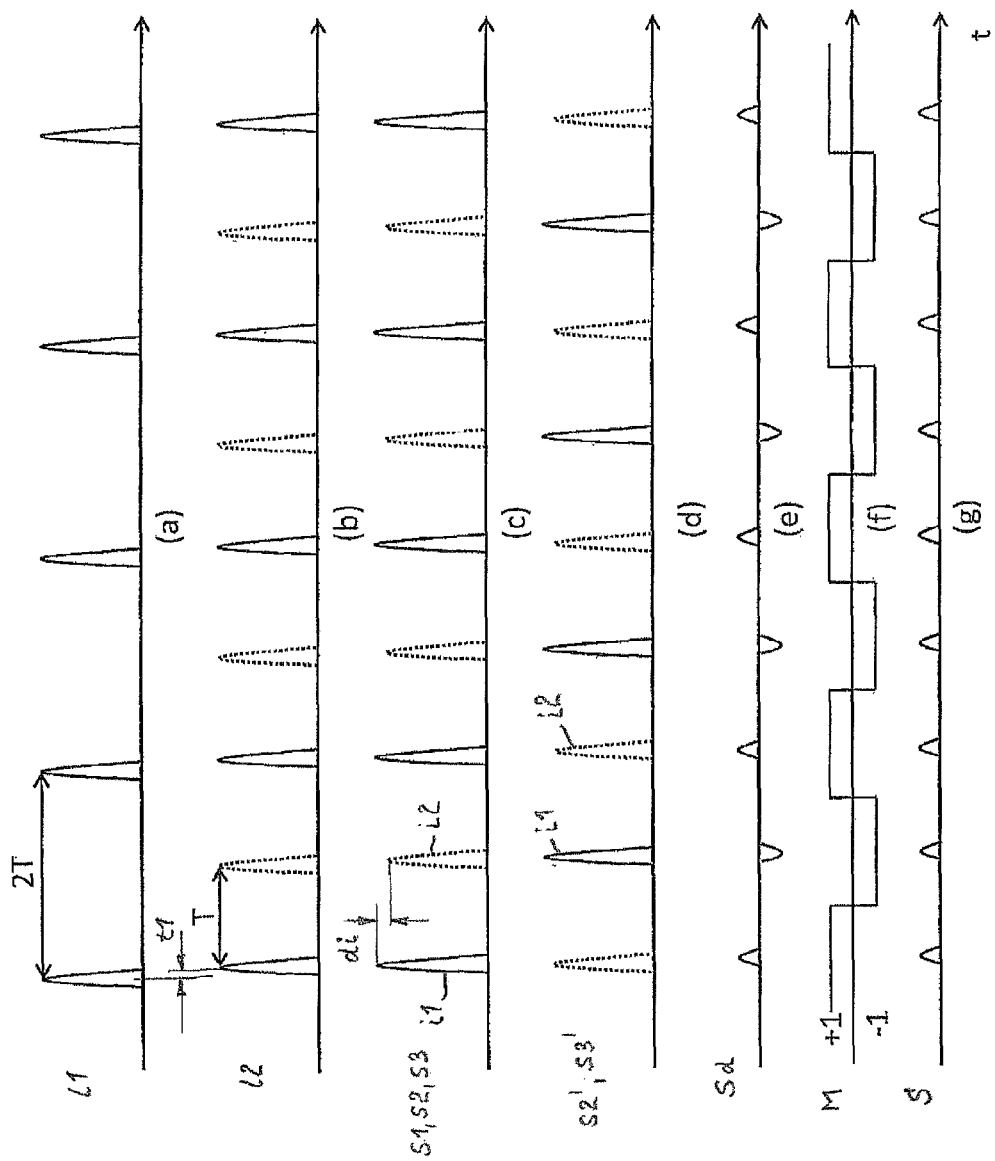
FIG. 2 shows associated signal curves.

In FIG. 1, an apparatus using a laser scanning microscope for imaging by means of stimulated fluorescence is illustrated. In FIG. 2, associated signal curves are illustrated, to which reference is made in the following description. Here, laser pulses I1, I2 of a first and second type have a different wavelength and are generated with identical repetition rate by means of two synchronized lasers, namely a first laser L1, also referred to as excitation laser, and a second laser L2 (probe laser). A synchronization device 10 serves for synchronization of the lasers L1, L2. The repetition rate of the first laser L1 is halved with the aid of a pulse picker 12 and output as laser pulses I1. Afterwards, both laser beams with laser pulses I1, I2 are combined in a beam splitter 14, preferably a dichroic beam splitter. Accordingly, a collinear beam is present then, which includes laser pulses I1 of the first laser L1 having half the repetition rate according to FIG. 2a with double time lag 2T and laser pulses I2 of the second laser L2 having the full repetition rate according to FIG. 2b with time lag T.

By way of an adjustable optical delay stage 15 it is guaranteed that later on at the sample P, the second laser pulse I2 of the second laser L2 arrives alternatingly with and without the other first laser pulse I1 of the first laser L1 preceding in time by a delay time t1, for example, less than one nanosecond. The signal S1 according to FIG. 2c measured at a detector D1 has alternatingly the intensity i1 of the second laser pulse I2 amplified by the stimulated fluorescence and increased by the amount di or, respectively the intensity i2 of the non-amplified second laser pulse I2.

After combining the two laser beams in the beam splitter 14, the light of the two lasers L1, L2 passes through a main beam splitter 16, arrives via intermediate optical systems, such as a beam expander telescope 18 illustrated representatively for various optical elements, at the scanning mirrors 20 of the confocal laser scanning microscope and, following a scan lens 22 and a tube lens 24, is directed onto the sample P via a microscope objective 26. Depending on whether a first laser pulse I1 with stimulated fluorescence belongs as a partner to the second laser pulse I2, the second laser pulse I2 is amplified in its intensity or not. The laser light passing through the sample P is collimated in a condenser 28 of the microscope, passed through a color cut-off filter 30 which blocks the light of the first laser L1 and is detected by means of the detector D1.

In addition to the light passing through the sample P, optionally or additionally the light backscattered by the sample P can be used for detection. To this end, between tube lens 24 and the objective 26 a motorized pivotable beam splitter 32 is located which, in the state in which it is pivoted into the beam path, couples out a part of the backscattered light from the main beam path and, after filtering out the light of the first laser L1 by means of color cut-off filter 34, directs it onto a further detector D2.

If the motorized beam splitter 32 is pivoted out of the beam path, then the backscattered light passes backwards through the tube lens 24, scan lens 22, scan mirrors 20, intermediate optical system 18 and is passed via the main beam splitter 16 of the microscope in the direction of the pinhole lens 36 of the confocal microscope which directs the light onto a confocal pinhole 38, downstream of which then likewise a detector unit D3 with upstream filters or a spectral detector unit (not illustrated) is arranged.

Independent of whether the detector D1, D2, D3 is located downstream of the sample P, upstream of the sample P or downstream of the detection pinhole 34 of the microscope, it is however always essential that second laser pulses I2 arrive at the detector D1, D2, D3 (see FIG. 2c) which are alternatingly amplified (i1) and not amplified (i2). Accordingly, at these locations similar or identical detector units having a similar or an identical evaluation can be used, the different versions of which are described in this and the following embodiments.

Preferably, the detectors D1, D2, D3 are photodiodes operated at bias voltage or avalanche diodes operated below the breakdown voltage or photomultipliers in linear operation. The bias voltage used in photodiodes serves here above all for increasing the response speed of the detectors. Correspondingly, small active detection zones are also advantageous, wherein, on the other hand, of course the size of the light spot to be detected has to be taken into account. The optical signal converted into an electric signal S1, S2, S3 according to FIG. 2c at the detector D1, D2, D3, is now split up into two branches Z1, Z2 at each of the detector D2 and detector D3, of which the one branch Z2 delays the signal S2 or, respectively, S3 with respect to the signal S2 or, respectively, S3 in the other branch Z1 electronically just by one pulse repetition rate T and the signals S2' and S3' are generated (see FIG. 2d). By way of electronic difference formation between the signal S2 or, respectively, S3 and the delayed signal S2' or, respectively, S3' in a differentiating element 40, one now obtains exclusively a difference signal Sd corresponding to the intensity of the stimulated fluorescence of interest, however with alternating sign according to FIG. 2e. By rectification of this signal Sd, preferably by way of electronic multiplication with an alternating mask signal M (FIG. 2f), one obtains at the output of a multiplication element 42 finally a signal S corresponding to the positive intensity of the stimulated fluorescence of interest (FIG. 2g), which is then finally digitized and further processed, for example, via a charge amplifier or fast analog-digital-converters. By assignment of the signals S corresponding to the measured intensities as a function of the position of the scan mirrors 20 to scanning points on the sample P, as a result a "map" of the sample P with respect to the respective stimulated fluorescence can be drawn and thus the technique of stimulated fluorescence can be used for microscopic imaging.

Figure 3:
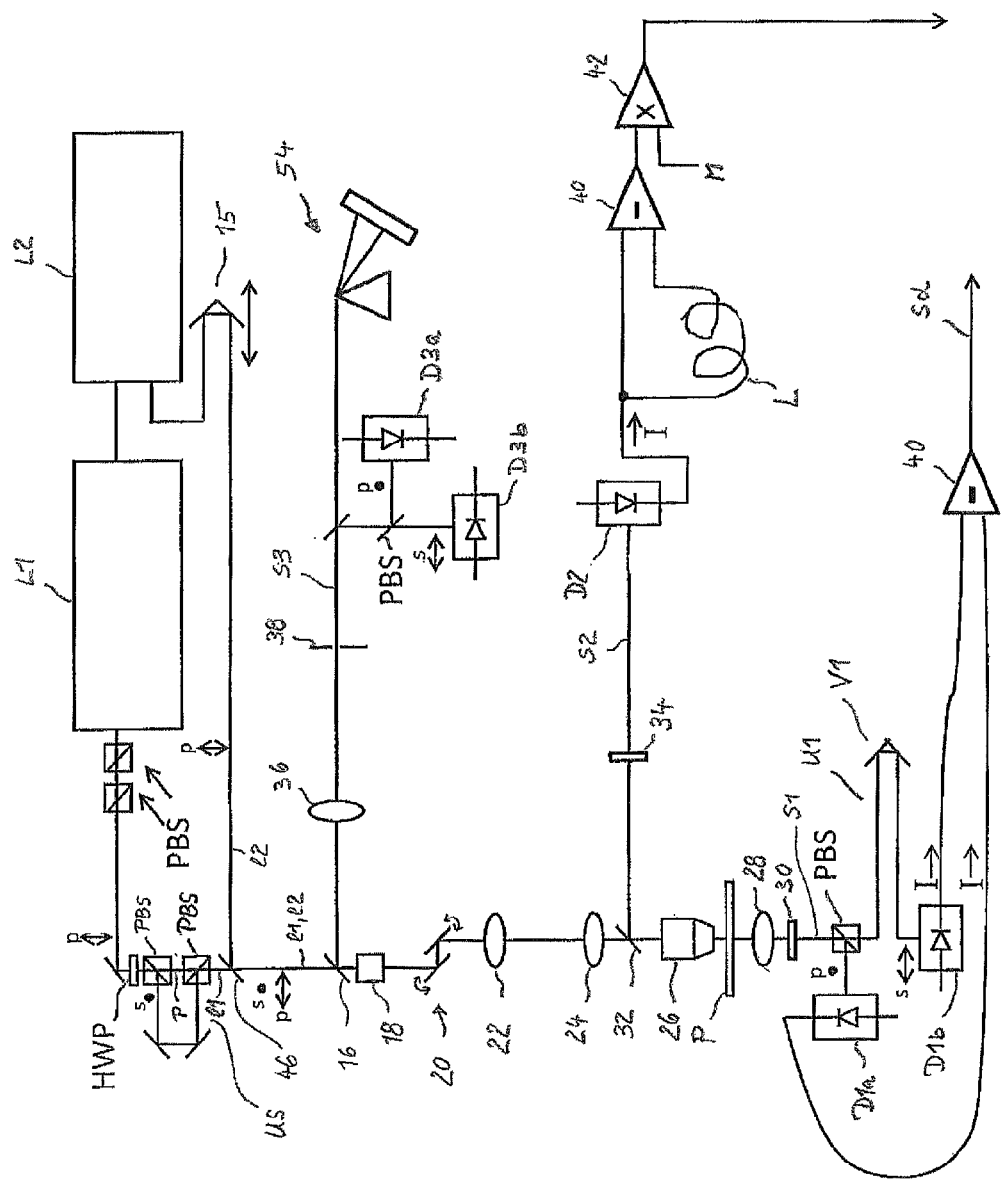
FIG. 3 shows an example with simultaneous first laser pulses and second laser pulses and the generation of intermediate pulses by means of a polarization device.

FIG. 3 shows another example having a different structure in which the inventive method is similarly used for imaging given stimulated Raman scattering, here exemplarily discussed on the example of "stimulated Raman loss". Parts that are identical to parts in the previous figures, are identified here and in the following with identical reference signs.

"Stimulated Raman loss" and also "stimulated Raman gain" dealt with further below, are processes related to stimulated fluorescence previously described, however, here, the simultaneous arrival, i.e. at the same time, of the laser pulses I1, I2 at the sample P is required. As is the case with stimulated fluorescence, in case of "stimulated Raman gain" an amplification of the second laser pulse I2 is observed when the first laser pulse I1 is simultaneously present at the sample P. In contrast thereto, in case of "stimulated Raman loss" the first laser pulse I1 is preferably detected. Given simultaneous presence of the second pulse I2, the first laser pulse I1 is slightly attenuated since the second laser pulse I2 takes away some of the intensity of the first laser pulse I1.

Given the apparatus according to FIG. 3 for making use of the "stimulated Raman loss" for an imaging in connection with a laser scanning microscope, as a first laser L1 a laser light source is used which uses the light of a wavelength in the range of 600 nm-1000 nm generated in an optical parametric oscillator (OPO). The second laser L2 uses as a laser light source the pump light of 1064 nm which pumps the first laser L1, i.e. pumps the OPO (OPO pump laser). Insofar, the two lasers L1, L2 are synchronized and have the same repetition rate T.

Figure 4:
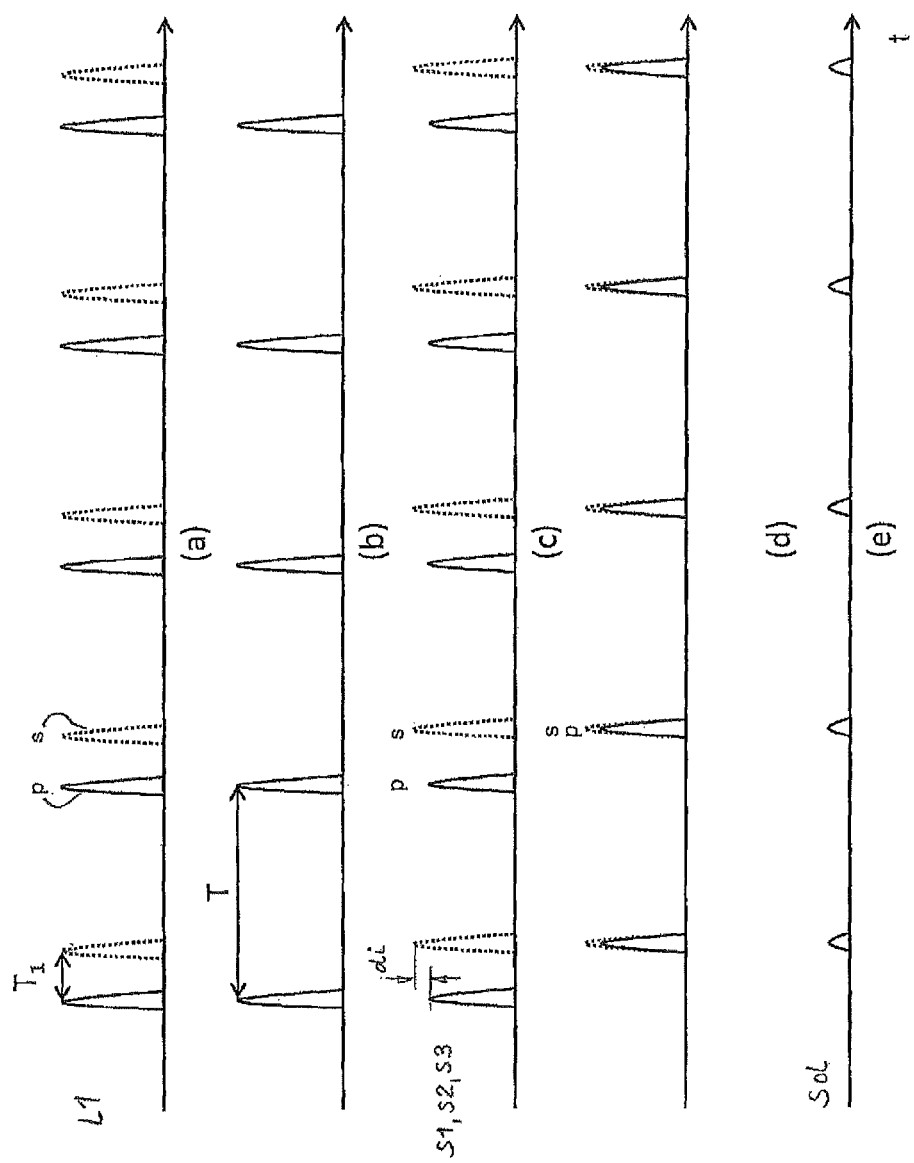
FIG. 4 shows associated signal curves.

In the present example according to FIGS. 3 and 4, another approach is chosen than in the example according to FIGS. 1 and 2. Instead of halving the repetition rate of the second laser L2, here additional laser pulses are inserted in the pulse sequence of the first laser L1. This takes place by beam splitting with detour path and subsequent re-combination of the pulses. Preferably, at first the light from the laser L1 is linearly polarized as good as possible with a sequence of polarization filters (PBS) so that the light has the polarization direction p parallel to a reference plane. With the aid of a motorized Lambda half wave plate, the polarization of the light is then rotated to 45° relative to the reference plane, for example, the table plane. As a result thereof, by means of a downstream polarization beam splitter PBS one achieves a splitting in halves of the light into the two main polarization directions, namely parallel p and perpendicular s to the reference plane. The light of the one polarization direction is guided via a detour path US for a temporal delay and subsequently, via a further polarization beam splitter PBS as a polarization combiner combined with the other partial beam. For generating greater temporal delays, the detour path US can also contain a glass fiber of predetermined length, e.g. with several meters of length. After passing through the polarization combiner the sequence of laser pulses I1 of the first laser L1 is comprised of the original pulses with p-polarization as well as pulses with s-polarization delayed by T1, which can thus be distinguished later on in the detection (see FIG. 4a). After this preparation of the first laser pulses I1, these are combined via a beam splitter 46, e.g. a dichroic color beam filter, with the second laser pulses I2 coming directly from the laser L2 (FIG. 4b), the temporal overlap being again guaranteed by a suitable optical delay stage 15.

After combining both types of laser pulses I1, I2, these are coupled into the laser scanning microscope at the main beam splitter 16, analogously to the first embodiment according to FIG. 1, and are directed onto the sample P via the various optical elements 20, 22, 24, 26. At the location of the sample P, now two situations occur alternatingly: when the first laser pulse I1 arrives at the sample P simultaneously with a second laser pulse I2, it is attenuated by an amount di according to the effect of "stimulated Raman loss" (see FIG. 4c). In the following pulse of the laser pulses I1 there is no loss according to "stimulated Raman loss", since no simultaneous second laser pulse I2 exists. Accordingly, after filtering out the second laser pulses I2 the signal S1, S2, S3 is comprised alternatingly of the signal attenuated by "stimulated Raman loss" as well as the non-attenuated signal (FIG. 4c). Since due to the selected arrangement, these two optical signals have a different polarization, they can be separated from one another with the aid of a polarization cube PBS2 and can be converted into electric signals in separate detectors.

After a suitable delay of the first of the two signals in a delay element V1, one obtains the signal curve illustrated in FIG. 4d. After difference formation of the two electric signals in the differentiating element 40, one obtains a difference signal Sd corresponding to the intensity of "stimulated Raman loss" as a background-free signal which can be made available to the image generating unit for further processing.

The required delay of the optical signals in the two polarization directions p and s, can either take place optically or, after conversion of the optical signals into electric signals, electronically. The optical delay is illustrated exemplarily with reference to the light passing through the sample P. Before the light hits one of the two detectors, it passes through an adjustable optical detour U1 so that the two optical signals are simultaneously converted into electric signals. It is however particularly advantageous when one achieves the delays electronically, e.g. by using adapted cable lengths. This is exemplarily illustrated with reference to the light back-scattered from the sample P, where a delay is obtained by an extended line L.

The difference formation of both detectors is particularly advantageously achieved in that photodiodes are used here which are connected to one another directly oppositely. Given an exact temporal match, the background signal currents compensate one another and there results an active current proportional to the signal of interest. The two photodiodes should be stabilized with respect to the temperature so far that no artifact signals arise given temperature drifts. Of course, it is advantageous here to mount the two photodiodes as close as possible on the same metallic carrier and to keep the electronic paths short.

In addition to the exact temporal synchronization of the two signal portions to be subtracted from one another an intensity match as exact as possible is likewise required. It can likewise take place optically or electronically. For an optical match, the motorized Lambda half wave plate described at the beginning is suited as a match element, possibly supported by a further, clearly finer motorized filter, such as a fine gray wedge, a neutral variable density filter or the like. For an electronic match, reference is made to respective electronic circuits. Particularly advantageously, the match is effected automatically. In this case, it is either matched with non-inserted sample P such that no detection signal is observed any more. Alternatively, it is matched such that the average signal or the minimum signal then has a fixed small value, preferably zero, given an inserted sample.

It has to be taken into account that in the present example the optical arrangement is chosen such that the two partial pulse sequences of laser L1 have different polarizations so that the arising optical signals can be separated from one another subsequently via polarization beam splitters. In certain situations it is, however, advantageous to use other optical properties instead of polarization. This can be, for example, the wavelength or also the direction or beam cross-section of the laser beam. Specifically, this would mean that the pulse sequence of a laser I is comprised of partial sequences of different wavelength, direction or beam cross-section. The separation takes place later on by means of a dichroic filter or a spatial filter instead of the polarization beam splitter cube PBS.

Figure 5:
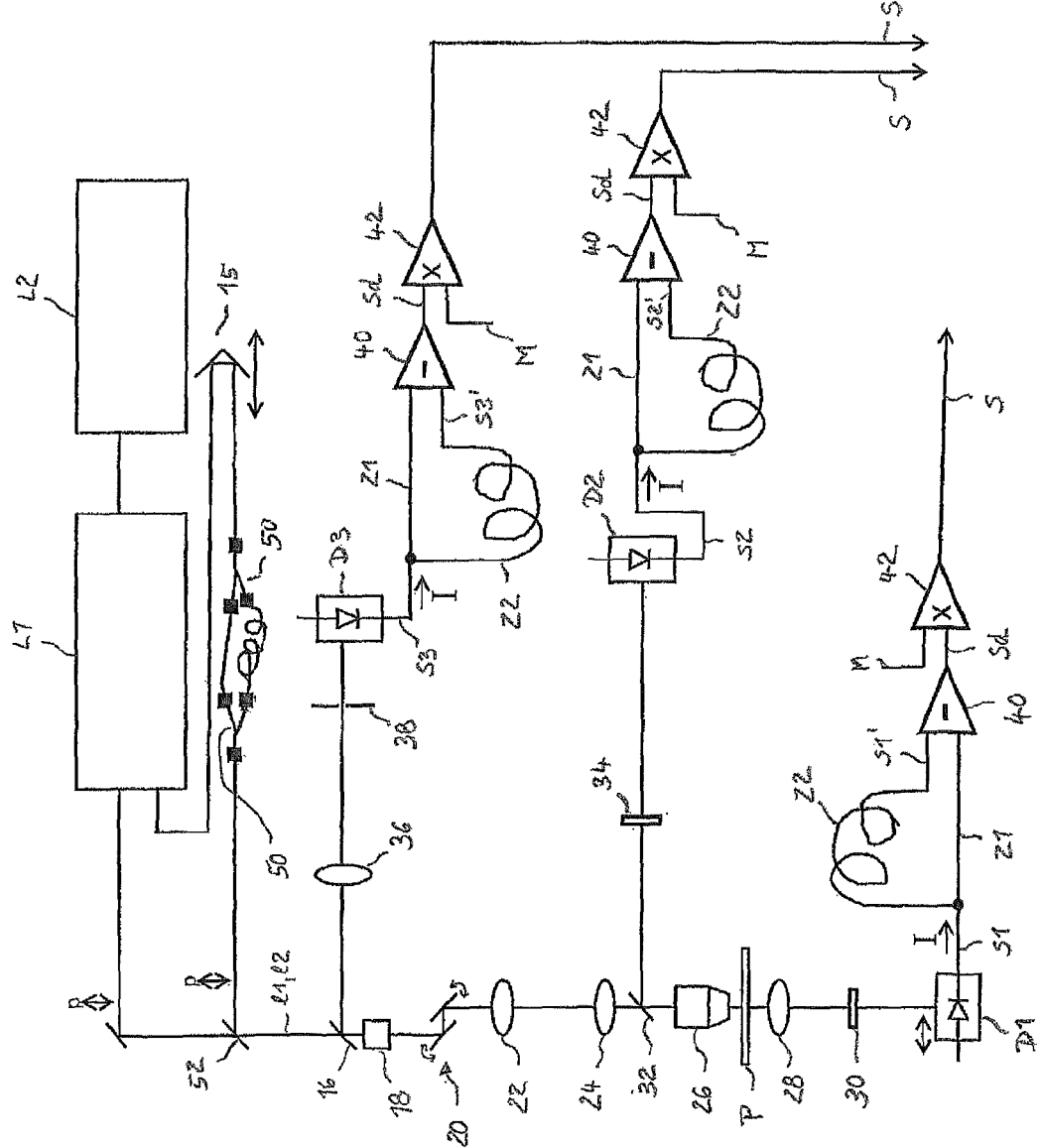
FIG. 5 shows a further example with simultaneous first and second laser pulses.
Figure 6:
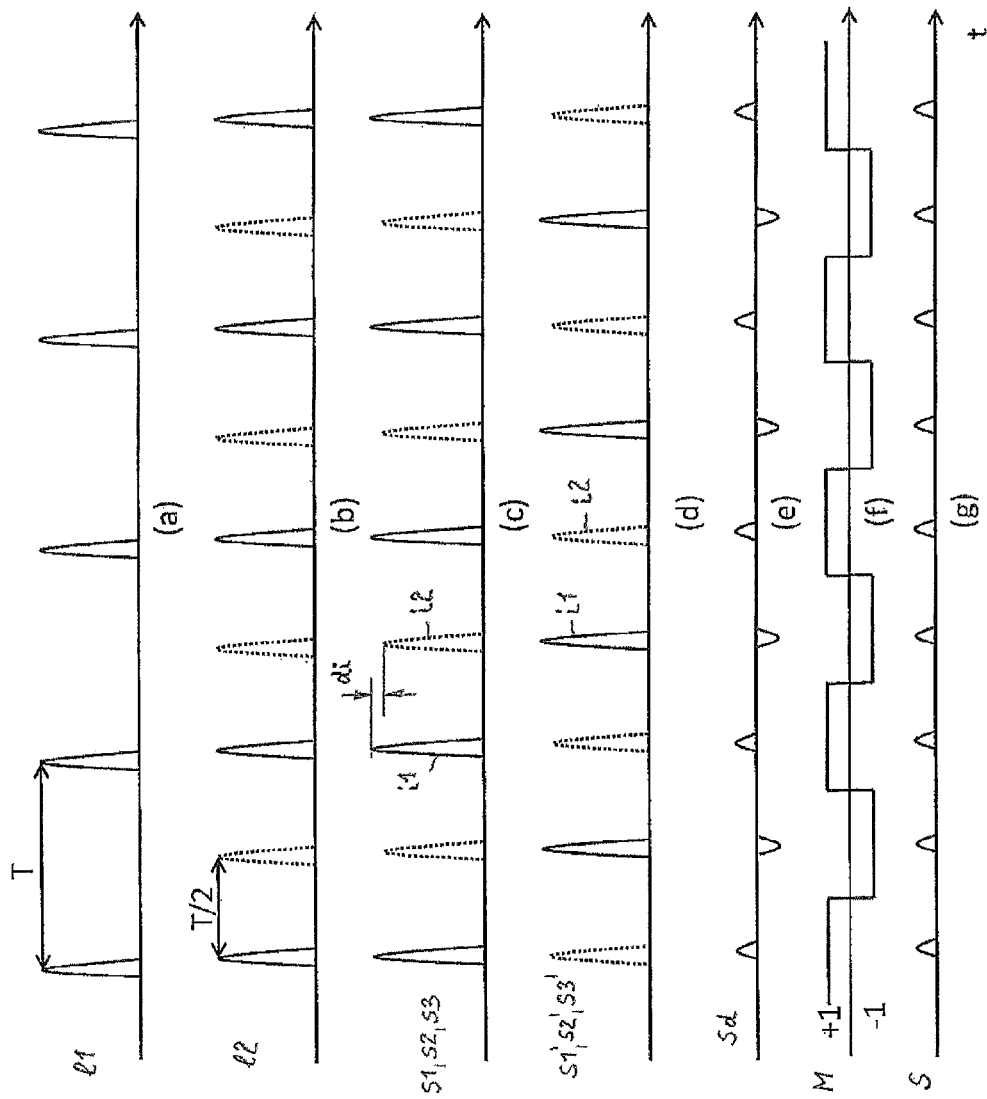
FIG. 6 shows associated signal curves.

FIG. 5 shows an embodiment making use of the "stimulated Raman gain" effect, which embodiment substantially corresponds to the embodiment according to FIGS. 1 and 2 for stimulated fluorescence, except that the first laser pulse I1 and second laser pulse I2 arrive exactly simultaneously at the sample P. In this embodiment, as a laser L1 the signal beam of an OPO (optical parametric oscillator) and as a laser L2 the idler beam of the same OPO is used. The temporal synchronization takes place via a suitable delay stage 15, which can, for example, also be realized fiber-optically. In the layout shown, the pulse sequence of the second laser L2 is now varied (FIG. 6b). This takes place analogously to the second embodiment, however, now a polarization rotation is dispensed with. The two branches of a Y fiber connector 50 present in duplicate with a short fiber and an elongated fiber for setting a delay are combined via a neutral beam splitter 52 instead via a polarizer. As a result thereof, certain light losses occur, however all pulses hit the sample with the same polarization through the optical systems. The arrangement for varying the pulse sequence of the second laser could, of course, again be comprised of a free beam optical system having the respective component parts such as beam splitter (preferably 50:50), delay stage and beam combiner (likewise preferably 50:50). As the respective realization is readily apparent to the person skilled in that art, an illustration thereof in every detail has been omitted. Instead, the fiber optical realization of the same situation is given, which uses instead of the free beam components the respective fiber optical components such as fiber Y coupler as beam splitters/combiners and glass fibers as a delay stage as well as fiber optical splicings as connecting elements.

The detection is again effected as in the first embodiment. So that the pulses newly inserted into the pulse sequence are actually located in the middle of the pulses of the original sequence, the delay stage 15 has to be correspondingly long. In order to be able to realize this with a compact design, preferably a delay stage 15 based on glass fibers is used. With respect to the signal curve and the signal evaluation, reference is made to FIG. 6, which substantially corresponds to FIGS. 2 and 4, so that the respective explanations made thereat can be called on for a detailed understanding.

The various embodiments can be combined with one another in manifold ways. For example, in the example according to FIG. 1 and FIG. 3, optical fibers can likewise be used for the delay stage 15. The generation of pulse sequences described in the example according to FIG. 3 can also be used for the examples according to FIG. 1 or FIG. 5. The rectification with the aid of the multiplier element 42 can also take place by a rapid phasing. The spectral detector unit 54 shown in FIG. 3, can also be used in the examples according to FIG. 1 or 5.

By replacing the first laser L1 with the second laser L2, the example of FIG. 3 can directly be applied to the use of "stimulated Raman gain" for imaging. Accordingly, the embodiment according to FIG. 5 explained further above can also be directly transferred to "stimulated Raman loss". The first embodiment, too, can also directly be used in connection with the stimulated Raman techniques, all further outlined techniques such as CARS, FM-CARS etc. as well as still other methods.

What is claimed is:

1. An optical evaluation method, comprising:
using one of stimulated fluorescence, stimulated Raman gain and stimulated Raman loss for generating a first optical signal and a second optical signal;
directing first laser pulses of a first type and second laser pulses of a second type that differs from the first type onto a sample to be examined;
hitting the sample with first incident light from the two laser pulses in at least one manner of simultaneously, within a very short time lag between the two laser pulses, and a time-correlated manner of the two laser pulses, thereby generating a first optical signal;
hitting the sample with second incident light from the two laser pulses in at least one manner of non-simultaneously, not within a very short time lag between the two laser pulses, and a non-time-correlated manner of the two laser pulses, thereby generating a second optical signal;
detecting the generated first and second optical signals with at least one detector; and
generating an electronic difference between the first and second optical signals.

2. The optical evaluation method according to claim 1, comprising:
generating the second laser pulses at a shorter repetition rate than the first laser pulses;
hitting the sample with the second laser pulses delayed by a predetermined delay time with respect to the first laser pulses;
feeding the second laser pulses to a detector; and
generating and evaluating the electronic difference between one of the second laser pulses and a subsequent second laser pulse.

3. The method according to claim 1, comprising:
hitting the sample simultaneously with the first laser pulses and the second laser pulses; and
generating and evaluating the electronic difference between one of the adjacent successive first and second laser pulses.

4. The method according to claim 1, comprising supplying the signals provided by the detector to an image processing unit.

5. The method according to claim 4, comprising providing the image processing unit in connection with a laser scanning microscope.

6. The method according to claim 4, comprising providing the image processing unit in connection with a confocal laser scanning microscope.

7. An apparatus for evaluating laser pulses in one of stimulated fluorescence, stimulated Raman gain and stimulated Raman loss for generating a first optical signal and a second optical signals, comprising:
a first laser that generates first laser pulses of a first type;
a second laser that generates second laser pulses of a second type that differs from the first type;
a light directing unit for directing the first laser pulses and the second laser pulses onto a sample to be examined, the light directing unit being configured to hit the sample with first incident light from the two laser pulses in at least one manner of simultaneously, within a very short time lag between the two laser pulses, and a time-correlated manner of the two laser pulses, thereby generating a first optical signal; and to hit the sample with second incident light from the two laser pulses in at least one manner of non-simultaneously, not within a very short time lag between the two laser pulses, and a non-time-correlated manner of the two laser pulses, thereby generating a second optical signal;
a first detector for detecting the generated first and second optical signals with at least one detector; and
an electronic signal processing unit generating an electronic difference between the first and second optical signals.

8. The apparatus according to claim 7, wherein
the first and the second laser are configured to generate the second laser pulses at a shorter repetition rate than the first laser pulses and to hit the sample with the second laser pulse delayed by a predetermined delay time with respect to the first laser pulses;
a second light directing unit is provided feeding the second laser pulses to a second detector; and
the electronic signal processing unit is configured to generate and evaluate the electronic difference between one of the second laser pulses and a subsequent second laser pulse.

9. The apparatus according to claim 7, wherein the first and the second laser are configured to generate the first laser pulses and the second laser pulses such that these hit the sample simultaneously, and the difference between successive pulses of one of the laser pulses is evaluated.

10. The apparatus according to claim 7, comprising an image processing unit for processing the signals provided by the detector.

11. The apparatus according to claim 10, comprising a laser scanning microscope.

12. The apparatus according to claim 11, wherein the laser scanning microscope is a confocal laser scanning microscope.

* * * * *